US007661957B2

(12) United States Patent
Tanimura

(10) Patent No.: US 7,661,957 B2
(45) Date of Patent: Feb. 16, 2010

(54) METHOD FOR REVERSIBLE FIXING OF A TOOL TO AN IMPLANTABLE ELEMENT AND DEVICE FOR CARRYING OUT SUCH A FIXING METHOD

(76) Inventor: Rémy Tanimura, 74 bis Boulevard Maurice Barrès, F-92200 Neuilly sur Seine (FR)

( * ) Notice: Subject to any disclaimer, the term of this patent is extended or adjusted under 35 U.S.C. 154(b) by 136 days.

(21) Appl. No.: 10/552,433

(22) PCT Filed: Apr. 1, 2004

(86) PCT No.: PCT/FR2004/000822

§ 371 (c)(1),
(2), (4) Date: Oct. 6, 2005

(87) PCT Pub. No.: WO2004/093714

PCT Pub. Date: Nov. 4, 2004

(65) Prior Publication Data

US 2006/0217738 A1 Sep. 28, 2006

(30) Foreign Application Priority Data

Apr. 16, 2003 (FR) .................................. 03 04731

(51) Int. Cl.
*A61C 8/00* (2006.01)
(52) U.S. Cl. ...................................... 433/173; 606/104
(58) Field of Classification Search ................ 433/163, 433/172, 173, 174; 606/104
See application file for complete search history.

(56) References Cited

U.S. PATENT DOCUMENTS

| 2,121,193 | A | * | 6/1938 | Hanicke ...................... 606/65 |
| 3,867,932 | A | * | 2/1975 | Huene ......................... 606/80 |
| 4,957,437 | A | | 9/1990 | Shimura |
| 5,195,891 | A | | 3/1993 | Sulc |
| 5,437,550 | A | * | 8/1995 | Beaty et al. .................. 433/141 |
| 5,569,037 | A | * | 10/1996 | Moy et al. ................... 433/173 |
| 5,690,639 | A | * | 11/1997 | Lederer et al. .............. 606/104 |
| 5,692,904 | A | * | 12/1997 | Beaty et al. .................. 433/141 |
| 5,702,398 | A | * | 12/1997 | Tarabishy .................... 606/232 |
| 5,720,751 | A | * | 2/1998 | Jackson ..................... 606/86 R |
| 5,947,733 | A | * | 9/1999 | Sutter et al. .................. 433/173 |
| 6,247,933 | B1 | * | 6/2001 | Wagner et al. .............. 433/173 |
| 6,328,746 | B1 | * | 12/2001 | Gambale ..................... 606/104 |
| 6,332,777 | B1 | | 12/2001 | Sutter |
| 6,488,501 | B1 | * | 12/2002 | Harding ...................... 433/173 |
| 7,160,109 | B2 | * | 1/2007 | Gervais et al. .............. 433/141 |
| 2003/0054319 | A1 | | 3/2003 | Gervais et al. |

FOREIGN PATENT DOCUMENTS

WO    WO 00/54696 A1    9/2000

* cited by examiner

*Primary Examiner*—Cris L Rodriguez
*Assistant Examiner*—Hao D Mai
(74) *Attorney, Agent, or Firm*—Oliff & Berridge, PLC

(57) ABSTRACT

A method for reversible fixing of a tool to an implantable element, when fitting of a dental prosthesis is performed, comprises, in a first step, reversible fixing of a hollow intermediate connecting part onto an external complementary part of the tool. In a second step, the method consists in placing the tool equipped with the intermediate connecting part, on the end of the implantable element until the intermediate connecting part clips onto an external complementary part of the implantable element. The hollow intermediate connecting part is preferably fixed by clipping or screwing onto the external complementary part of the tool.

20 Claims, 17 Drawing Sheets

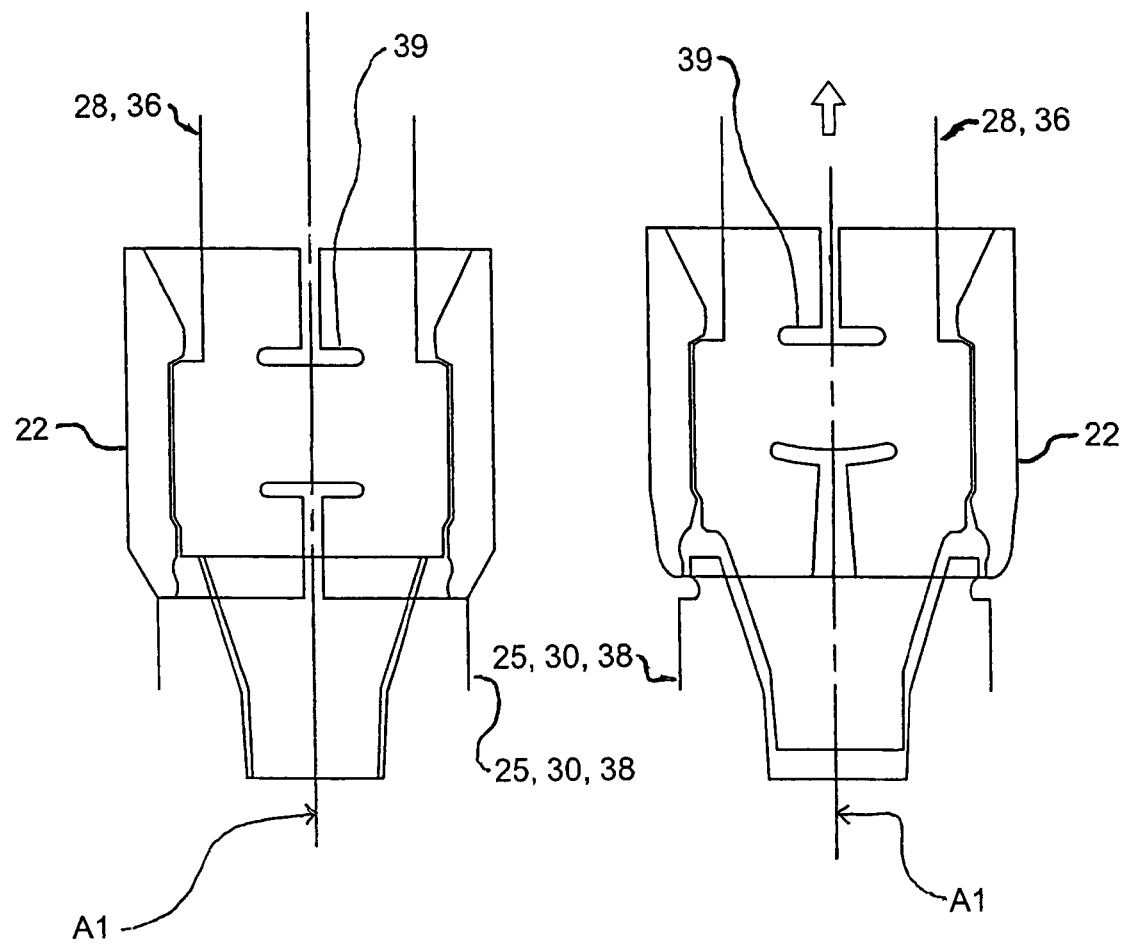

METHOD FOR REVERSIBLE FIXING OF A TOOL TO AN IMPLANTABLE ELEMENT AND DEVICE FOR CARRYING OUT SUCH A FIXING METHOD

BACKGROUND OF THE INVENTION

The invention relates to a method for reversible fixing of a tool to an end of an implantable element, when fitting thereof and for achievement of a dental prosthesis, and to a device for implementing of such a method.

STATE OF THE ART

Fitting an implanting prosthesis consists mainly in implanting an artificial root in the maxillary or the mandible of a patient, of making an imprint of the location of the dental root so as to then manufacture the final dental prosthesis and to place the latter on the artificial root. The artificial root also called dental implant is designed to support either a pillar forming an artificial stump on which a dental prosthesis is sealed, or an intermediate pillar onto which the dental prosthesis is screwed. The prosthesis can also be screwed directly onto the dental implant. In the course of these different steps, the practitioner has to use numerous tools that are hardly practical to fix onto the implantable elements.

The dental implant generally has the form of a screw (FIGS. 1 and 3), preferably cylindrical and provided with an external thread 2 designed to screw the dental implant 1 into the bone tissues. One of the ends of the screw forms a head 3 provided with a bore extending the external thread, the bore and head 3 forming an anti-rotational system preventing rotation of the part or of the tool fixed to the implant and which can be external (FIG. 1) or internal (FIG. 3). It comprises an internal thread 4 extending partly into the shank of the screw. The internal thread 4 enables a tool or a prosthetic part such as a pillar to be fixed to the dental implant.

Thus, to fit the dental implant 1 in a patient's jaw, the practitioner uses a tool supporting the dental implant 1. This tool, also called implant holder 5, is fixed to the implant 1, most of the time by a screw 6 (FIGS. 2 and 4). The implant 1 can be screwed into the bone by means of a motor. It is then necessary to fix the implant holder 5 on a mandrel 7 by means of O-rings 8. This type of fixing does however present drawbacks. Indeed, once the dental implant 1 has been placed in the jaw, the implant holder 5 still has to be unscrewed. In addition, the assembly formed by the mandrel 7, the implant holder 5 and the implant 1 is cumbersome and requires the patient's mouth to be very wide open.

After an osteo-integration period, the practitioner makes an imprint in order to determine the location and orientation of the dental implant (or of the intermediate pillar) precisely for manufacturing of the final dental prosthesis. The imprint is achieved by means of a transfer part which is fixed, in a first step, to the dental implant (or to the intermediate pillar). Then a reproduction of the implant, called a laboratory analogous part or die, is fixed onto the transfer part which is imprisoned in the imprint material, the reproduction being designed to subsequently represent the implant or the intermediate pillar in the plaster model cast according to the imprint.

Two main techniques exist for taking imprints. The first technique for taking imprints, called the Pick-up technique, consists in using a perforated imprint holder in which an imprint material is cast and which enables the screw fixing the transfer part to the implant to be cleared and unscrewed. Once the imprint has been removed, the transfer part is imprisoned in the imprint material and the end of the transfer part can then be screwed onto the die. The die is then cast in an imprint material so as to form a working model acting as support to achieve the final dental prosthesis. This technique is relatively reliable and precise, but it can prove difficult to implement depending on the location of the implant. The second technique, called the Pop-in technique, differs from the first technique by the fact that a closed imprint holder is used and that the transfer part is repositioned in the imprint material once the latter has been removed from the dental implant. This technique is relatively simple and quick, but it can prove imprecise, in particular due to the repositioning of the transfer part in the imprint holder.

Fixing of the transfer part onto the implant or onto the die is generally performed by screwing, which makes positioning and removal of the transfer part difficult to implement. In the document WO-01/64127, it has been proposed to use a transfer part suited to the Pick-up technique. The transfer part comprises a body extended by one or more deformable branches designed to clip into the head of a dental implant. Clipping of the transfer part into the dental implant is however not satisfactory, as impurities may get into the deformable branches of the transfer part and are liable to block the transfer part in the dental implant, preventing removal thereof.

The prosthetic parts and tools used when fitting a dental prosthesis are generally suitable for a single function. Their number and the different connection systems make fitting of the dental prosthesis long and can lead to handling errors. They can in particular cause safety problems, the patient being liable to ingest small parts and/or tools during the operations.

A range of toolings used in dental implantology has been proposed, in the document WO-0207638, for which the working part of a tool is fixed, in reversible manner, to the rest of the tool so as to be able to be changed, fixing being able to be performed by clipping. This technique only enables the practitioner to use the common base of the tool for several identical operations. It therefore does not make the different steps of fitting a dental prosthesis easier. The document U.S. Pat. No. 6,332,777 also describes direct and reversible fixing of a tool such as an impression element also called printing or casting cap on an implantable element, which can for example be an implant. The implant thus comprises an implantable part designed to be implanted in a bone or in a model, a head designed to faire be salient from the bone or model and a shoulder arranged between the head and the implantable part. Fixing of the printing element on the implant is then performed by means of fixing means arranged at one of the ends of the printing element and designed to be engaged in the shoulder of the support.

Moreover, intermediate connecting parts exist permanently fixing two implantable elements designed to remain in a patient's jaw. Thus, the document U.S. Pat. No. 4,957,437 describes an artificial tooth comprising a contact element, a hollow metal base element arranged inside the contact element, a metal pillar arranged in the hollow of the base element and elastic buffer elements arranged in a space formed between the base element and the pillar. The pillar and the top part of the base element respectively comprise recesses designed to receive one of the buffer elements. The buffer element enables a satisfactory damping effect to be obtained between the pillar and the base element while ensuring permanent connection between the pillar and base element, i.e. between two elements designed to remain in a patient's jaw.

Such an element is however not suitable for reversible fixing of tools onto implantable elements.

OBJECT OF THE INVENTION

It is an object of the invention to propose a method for fixing between tools and implantable elements that is reliable, practical, quick to implement, and suitable for different types of tools and implantable elements used during the different steps of fitting of the dental implant and for achieving a dental prosthesis.

According to the invention, this object is achieved by the fact that the method for fixing successively comprises:
- reversible fixing of a hollow intermediate connecting part onto an external complementary part of the tool,
- positioning of the tool equipped with the intermediate connecting part on the end of the implantable element until the intermediate connecting part clips onto an external complementary part of the implantable element.

It is also an object of the invention to provide a device for implementation of such a method, reducing the risk of ingestion of tools or parts used during fitting of the dental implant and for achieving a dental prosthesis and facilitating the steps of such a fitting.

This object is achieved by the fact that the device comprises a hollow intermediate connecting part comprising fixing means for fixing the connecting part in reversible manner onto an external complementary part of the tool, and clipping means designed to clip into an external complementary part of the implantable element, so as to enable reversible fixing of different types of tools in different types of implantable elements.

According to a development of the invention, the fixing means comprise at least one groove formed in the internal wall of the connecting part and designed to cooperate, by clipping, with a salient peripheral rib on the tool.

According to a first preferred embodiment, the groove is delimited by at least one rim arranged at one end of the connecting part, said rim being designed to cooperate, by clipping, with an external groove formed at the end of the implantable element.

According to a second preferred embodiment, the clipping means comprise a second groove formed in the internal wall of the connecting part and designed to cooperate with an external rib formed at the end of the implantable element.

BRIEF DESCRIPTION OF THE DRAWINGS

Other advantages and features will become more clearly apparent from the following description of particular embodiments of the invention given as non-restrictive examples only and represented in the accompanying drawings, in which.

Figure 7:
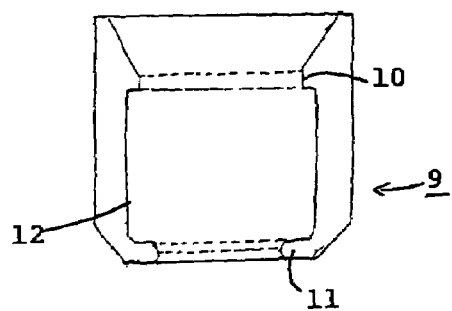

The FIG. 7 schematically represents an intermediate connecting part according to the invention.

Figure 5:
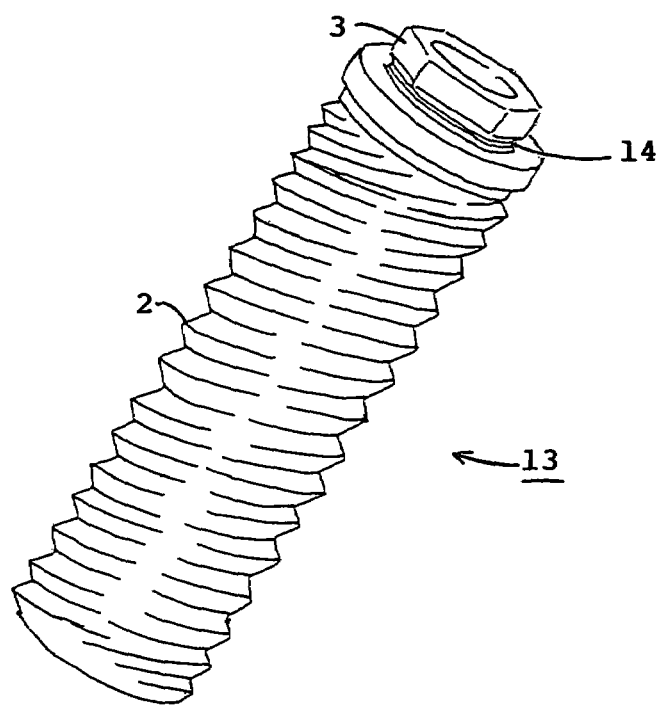
FIGS. 5 and 6 are respectively a perspective view and a cross-sectional view of a dental implant with an external head according to the invention.
Figure 8:
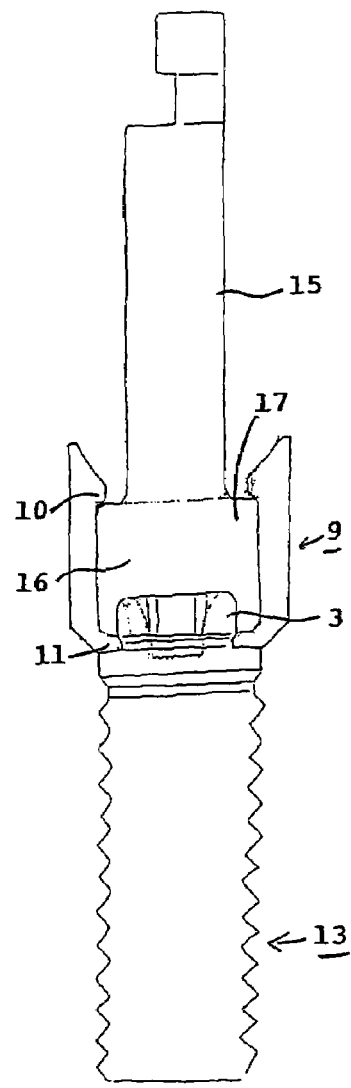
Figure 9:
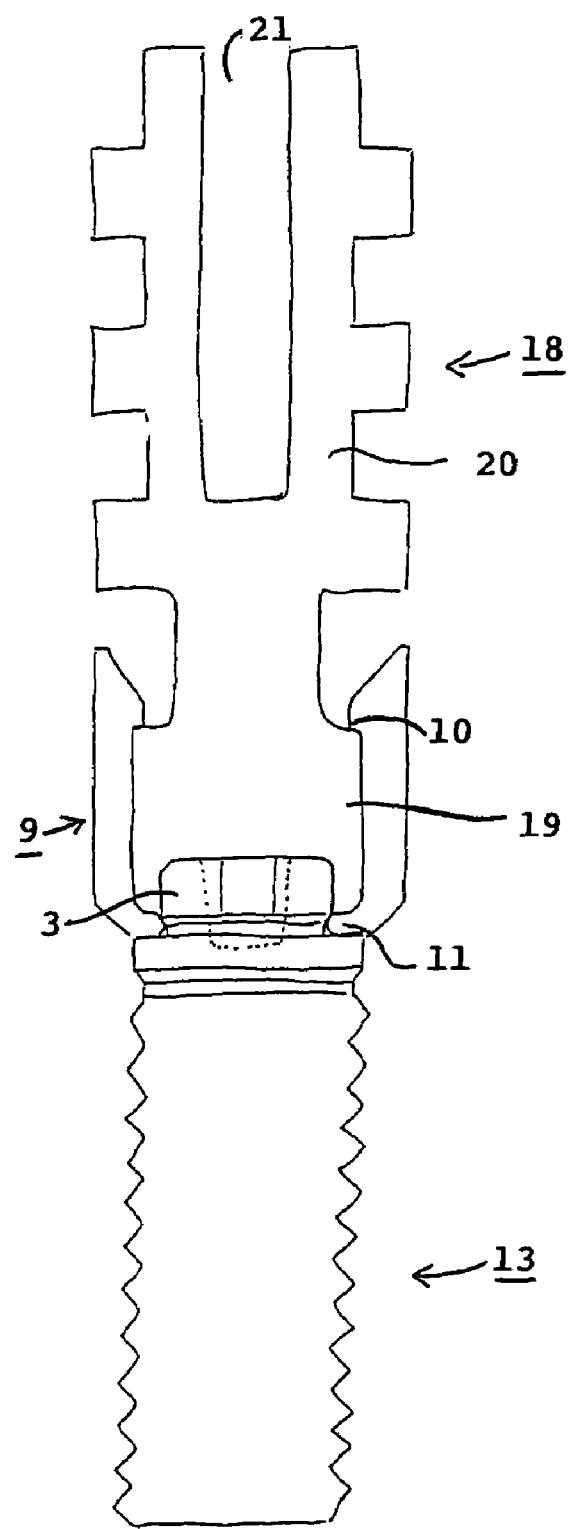

FIGS. 8 and 9 respectively represent a placing tool and a transfer part respectively fixed onto the dental implant according to FIG. 5.

Figure 10:
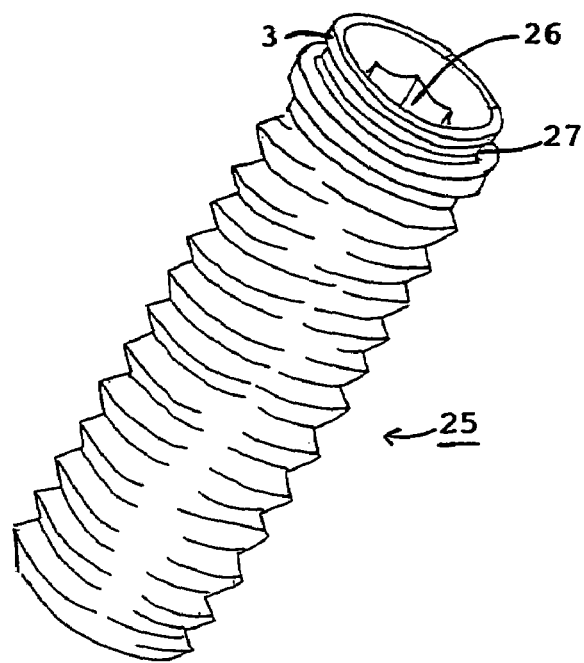
Figure 11:
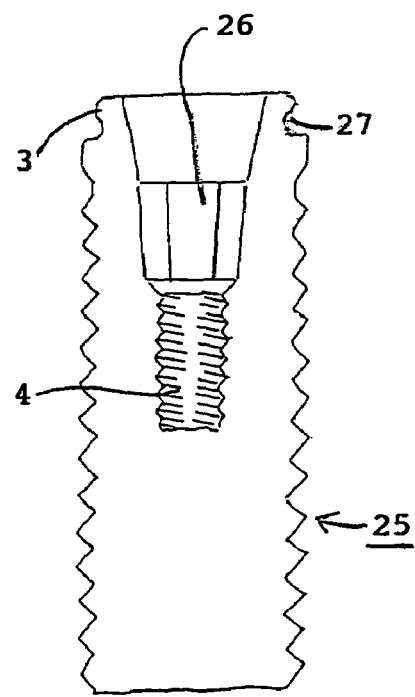

FIGS. 10 and 11 are respectively a perspective view and a cross-sectional view of a dental implant with an internal head according to the invention.

Figure 12:
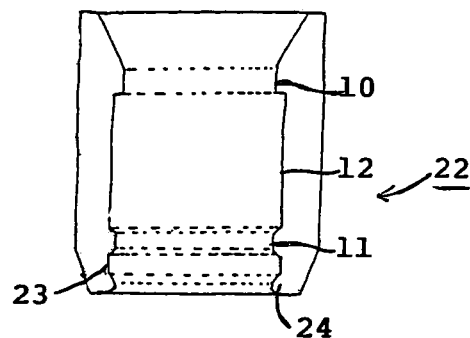

FIG. 12 schematically represent an intermediate connecting part according to the invention.

FIGS. 13 to 20 schematically represent tools fixed onto an implantable element according to the invention.

FIGS. 21 to 25 represent different embodiments of an intermediate connecting part according to the invention.

Figure 26:
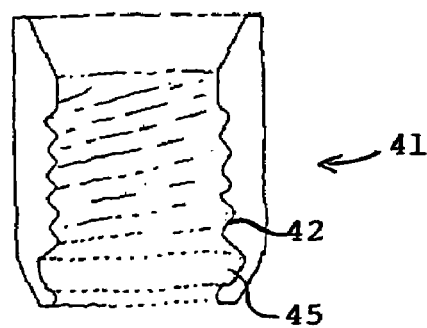
Figure 27:
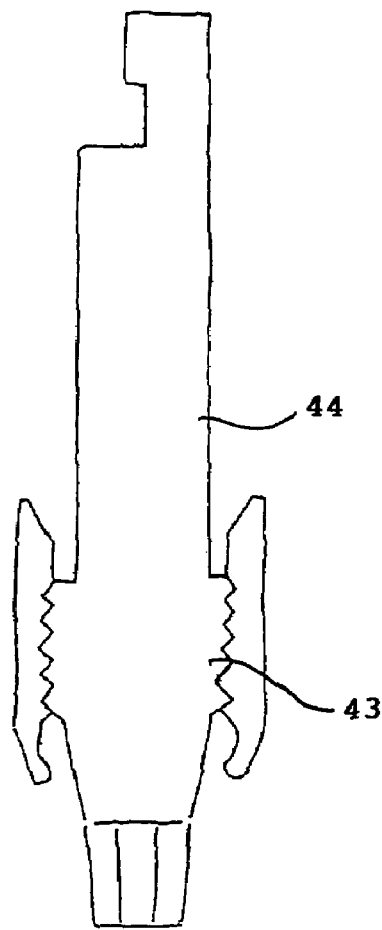

FIGS. 26 and 27 respectively represent a particular embodiment of an intermediate connecting part according to the invention and a tool equipped with such a connecting part.

DESCRIPTION OF PARTICULAR EMBODIMENTS

A method for fixing a tool to an end of an implantable element when a dental prosthesis is fitted consists in fixing different types of tools in reversible manner onto different types of implantable elements. For this, a hollow intermediate connecting part is designed to be fixed, in reversible manner, by screwing or clipping, onto an external complementary part of the tool and by clipping onto an external complementary part of the implantable element. The intermediate connecting part is sterile and generally used once only, i.e. it is proper to a patient. The same intermediate connecting can in fact be used several times for the same patient. The connecting part is designed to deform in an elastic manner when clipped on. It can thus be made of plastic material such as a Teflon® type fluorine polymer or Nylon®. The connecting part can also be made of metal, for example of titanium or titanium alloy. In this case, the connecting part comprises slots enabling the metal connecting part to deform. It can also comprise a part made of plastic and a part made of metal.

By implantable element, what is meant is an element acting as artificial root for the dental prosthesis and designed to be implanted in a patient's jaw, such as a dental implant or an intermediate pillar designed to be fixed onto a dental implant. Such an implantable element is preferably titanium-based so as to favour a good osteo-integration between the bone tissues of the jaw and the implant. It can thus be made of pure titanium or titanium, aluminium and vanadium-based alloy. By implantable element, what is also meant is a reproduction of a dental implant, also called laboratory analogous part or die and designed to form the laboratory model used to manufacture the dental prosthesis.

By tool, what is meant is an instrument used when fitting an implantable element, such as an implant holder, a pillar holder, or a mandrel, but also the transfer part used for manufacturing the dental prosthesis.

According to a first embodiment represented in FIG. 7, a substantially cylindrical and hollow intermediate connecting part 9 comprises an internal wall in which first and second rims 10 and 11 are formed. The first and second rims 10 and 11 are salient towards the inside of the connecting part 9 and they are each arranged at one end of the intermediate connecting part 9. The first and second rims 10 and 11 delimit a groove 12 designed to cooperate with an external complementary part of a tool. The connecting part intermediate 9 is thus designed to be placed on a tool to fix the tool in reversible manner onto an implantable element.

Figure 1:
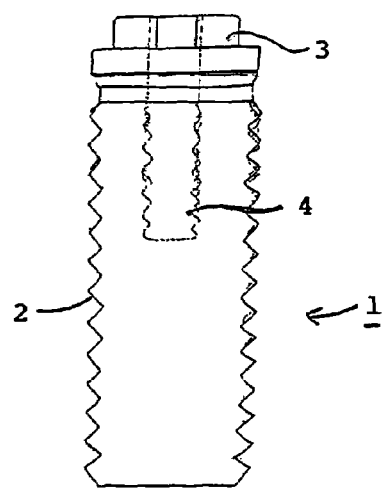
FIG. 1 is a cross-sectional view of a dental implant with an external head according to the prior art.
Figure 6:
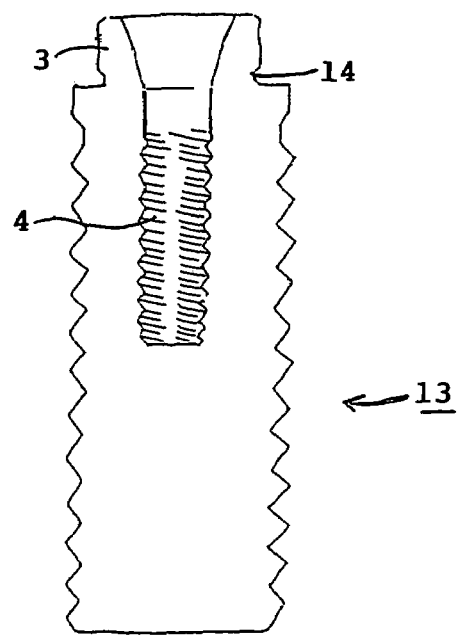

The implantable element can for example be a dental implant 13 with an external anti-rotational system such as that represented in FIGS. 5 and 6. The dental implant 13 has a shape substantially equivalent to that of the dental implants 1 with external anti-rotational system according to the prior art (FIG. 1), the head 3 however comprising, at its external periphery, an external groove 14 acting as external complementary part for clipping of the connecting part 9 onto the dental implant 13. In FIGS. 5 and 6, the dental implant 13 has a hexagonal anti-rotational system.

Thus, to place such a dental implant 13 in a patient's jaw, the practitioner fixes the connecting part 9, by deformation followed by clipping, onto the distal part 16 of a placing tool 15 acting as a mandrel (FIG. 8). The dental implant can be screwed into a patient's jaw by means of the placing tool, either by means of a motor or manually. The distal part 16 of the placing tool 15 has a complementary shape to the internal wall of the connecting part 9, so as to clip the connecting part perfectly around the placing tool 15. It thus comprises a salient peripheral rib 17 designed to cooperate in the groove 12 of the connecting part 9. The complementarity of the shapes of the distal part 16 and of the internal wall of the connecting part 9, and fixing by clipping, prevent vertical movements of the placing tool inside the connecting part 9.

The end of the distal part 16 of the placing tool 15 also comprises an opening having a complementary shape to that of the head 3 of the dental implant 13. Thus, once the placing tool 15 has been equipped with the connecting part 9, the practitioner places the opening of the placing tool 15 on the head 3 of the dental implant 13 until the second rim 11 of the intermediate connecting part clips into the external groove 14 of the dental implant 13. Reversible fixing of the placing tool 15 on the dental implant 13 is thus achieved by clipping of the connecting part 9 onto the dental implant.

Figure 2:
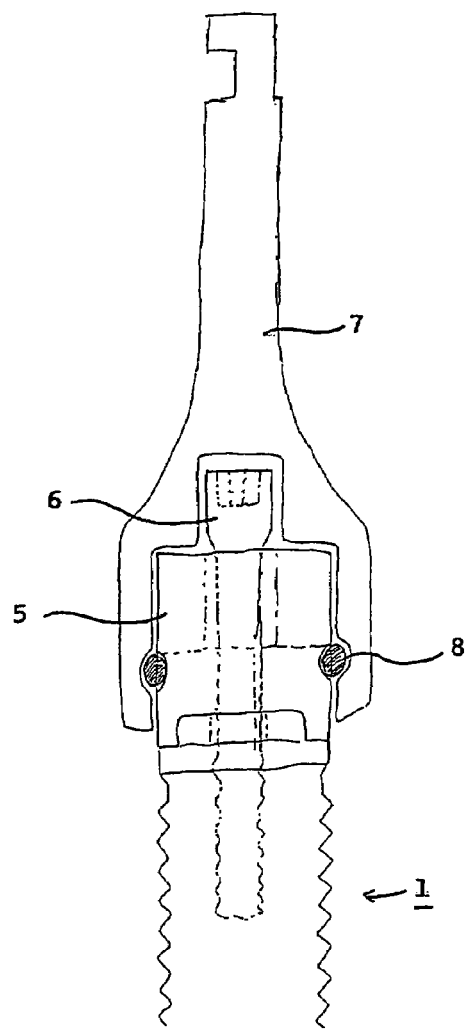
FIG. 2 is a cross-sectional view of a placing tool according to the prior art, fixed to the dental implant according to FIG. 1.

The assembly formed by the intermediate connecting part 9 and the placing tool 15 advantageously replaces the implant holder and mandrel according to the is prior art (FIG. 2). Indeed, a slight pressure enables the placing tool 15 to be fixed, by means of the intermediate connecting part, onto the head 3 of the dental implant 13, whereas to remove the placing tool, it suffices to pull slightly to release the dental implant 13. The intermediate connecting part 9 thus avoids screwing and unscrewing operations which require a special tool and a sufficiently large opening of the mouth to have access to the screw which fixes the implant holder according to the prior art to the dental implant.

Once they have been clipped together, the tool and the connecting part and the connecting part and the dental implant are in intimate contact, without any clearance. Thus, no partial clipping should be observed, either the assembly has no clearance or the connecting part and the dental implant are unclipped.

As represented in FIG. 9, the intermediate connecting part 9 also enables reversible fixing to be performed between the dental implant 13 and a transfer part 18. The transfer part can be of any known type. It however comprises a distal part designed to be fixed to the dental implant 13 and then to a die (not represented). The distal part of the transfer part 18 has the same shape as that of the placing tool 15. It thus comprises an opening having a complementary shape to that of the head 3 of the dental implant, and it comprises a salient peripheral rib 19 designed to cooperate with the groove 12 of the connecting part 9. It also comprises a proximal part 20 provided with two perpendicularly crossing slots 21.

Such a fixing in particular enables an imprint to be made with a closed imprint holder such as those used for the technique called Pop-in, while preserving the reliability and precision of the technique called Pick-up. Connection between the connecting part and the dental implant or the die is thus easy to perform and avoids numerous screwing and unscrewing operations. In addition, performing external clipping prevents contact between the distal part of the tool and the tissues of the patient's jaw. The tool is thus not liable to be contaminated by peri-implanting tissues.

In a second embodiment represented in FIG. 12, the intermediate connecting part 22 comprises an internal wall wherein adjacent first and second grooves are formed, the first groove 12 being much wider than the second. The first groove 12 is delimited by the first and second rims 10 and 11, whereas the second groove 23 is delimited by the second rim 11 and by a third rim 24 extending the end of the connecting part designed to be fixed to the end of the implantable element.

Figure 3:
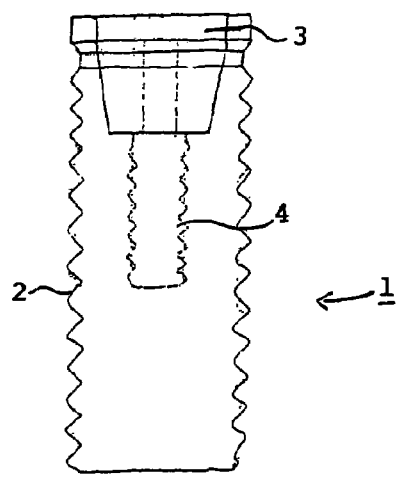
FIG. 3 is a cross-sectional view of a dental implant with an internal head according to the prior art.
Figure 4:
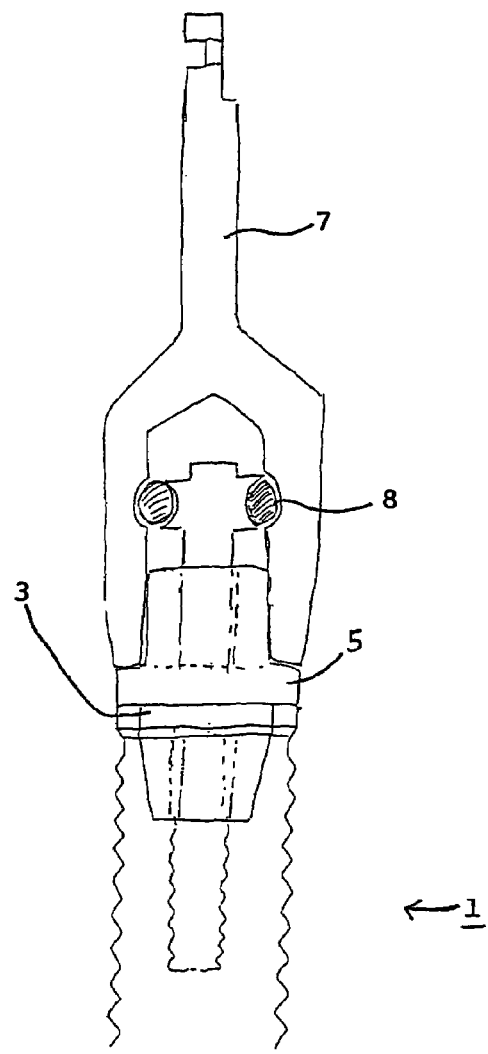
FIG. 4 is a cross-sectional view of a placing tool according to the prior art, fixed to the dental implant according to FIG. 3.

The implantable element can for example be a dental implant with an internal anti-rotational system and designed to be placed in a patient's jaw, such as that represented in FIGS. 10 and 11. The dental implant 25 has a substantially equivalent shape to that of the dental implants with an internal anti-rotational system according to the prior art (FIG. 3). The internal anti-rotational system has the shape of a hexagon in FIGS. 10 and 11. Thus, the dental implant 25 comprises a head 3, a bore 26 opening out onto one end of the dental implant. The bore 26 forms the internal anti-rotational system of the dental implant 25 and it is extended by an internal thread 4. The end of the dental implant is provided, at the external periphery thereof, with at least one external rib 27 acting as external complementary part for clipping the connecting part 22 onto the dental implant 25.

Figure 13:
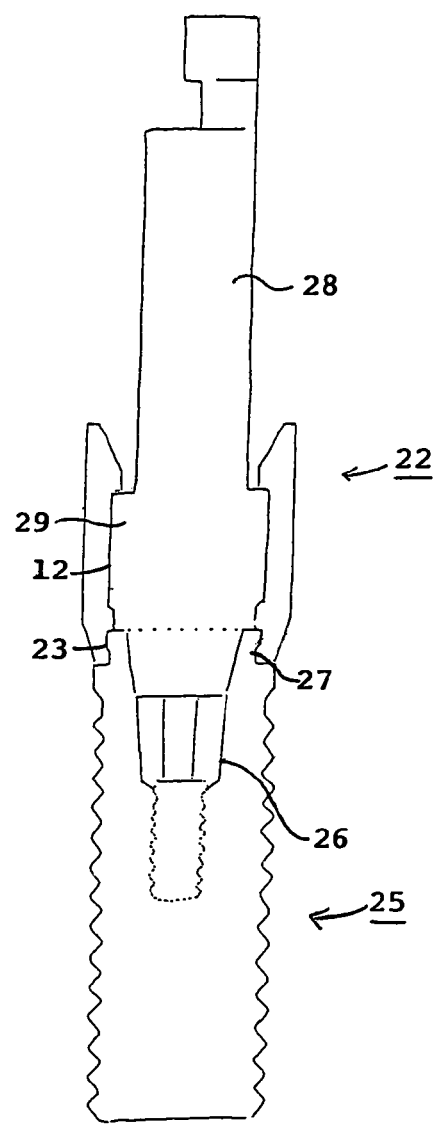
Figure 14:
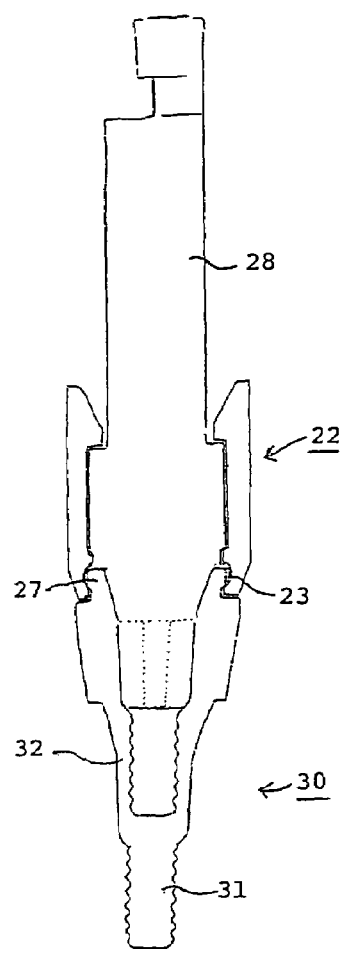

In FIG. 13, the connecting part 22 is placed, by elastic deformation followed by clipping, around a placing tool acting both as implant holder and as mandrel. Thus, in a similar way to the first embodiment, the placing tool 28 comprises an external complementary part 29 designed to cooperate with the first groove 12 of the connecting part 22 when the latter is clipped onto the placing tool 28. Once the connecting part has been placed on the placing tool 28, the end of the placing tool 28 is inserted in the bore 26 of the dental implant 25, until the external rib 27 of the dental implant 25 clips into the second groove 23 of the connecting part. The end of the placing tool 28 has a complementary shape to the bore 26 of the dental implant 25.

Figure 15:
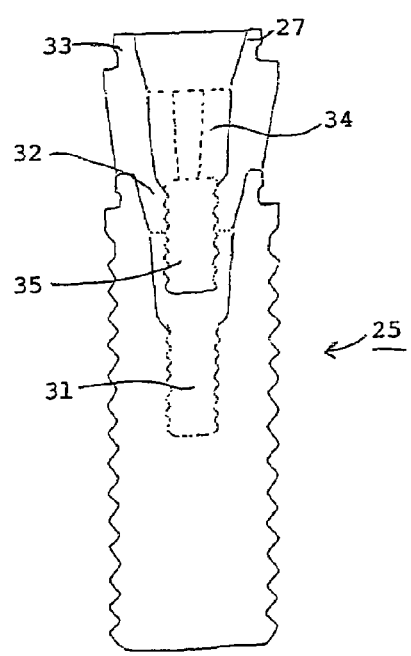

The intermediate connecting part 22 can also fix a placing tool in reversible manner to an intermediate pillar, in particular to place the latter in a dental implant 25 with an internal anti-rotational system such as that represented in FIGS. 10 and 11. Thus, in FIG. 14, the placing tool 28 used to place the dental implant 25 in a patient's jaw is equipped with the connecting part 22 and it is then fixed in reversible manner to an intermediate pillar 30. The intermediate pillar 30 is designed to be fixed by screwing into the dental implant 25 (FIG. 15). For this, it comprises a threaded end 31, a body 32, a head 33 and a bore 34 forming an anti-rotational system, the bore 34 being extended by an internal thread 35. The body 32 is of suitable shape to be able to be inserted into the bore 26 of the dental implant without using the anti-rotational system of the bore 26 of the dental implant. The head 33 comprises an external rib 27 similar to that of the dental implant 25. Thus, the placing tool 28 is fixed to the intermediate pillar by means of the connecting part 22. The assembly is then placed on the end of the dental implant 25 (FIG. 15), so as to place the intermediate pillar in the dental implant 25. The placing tool 28 equipped with the connecting part 22 is then removed from the intermediate pillar 30 after the latter has been screwed into the dental implant 25. Handling of the intermediate pillar is thus performed with the same placing tool 28 as for fitting of the dental implant. This enables the risks of losing the pillar by ingestion to be reduced and prevents any contamination when handling. The fixing method also enables the operating time to be reduced and it is economical.

Figure 16:
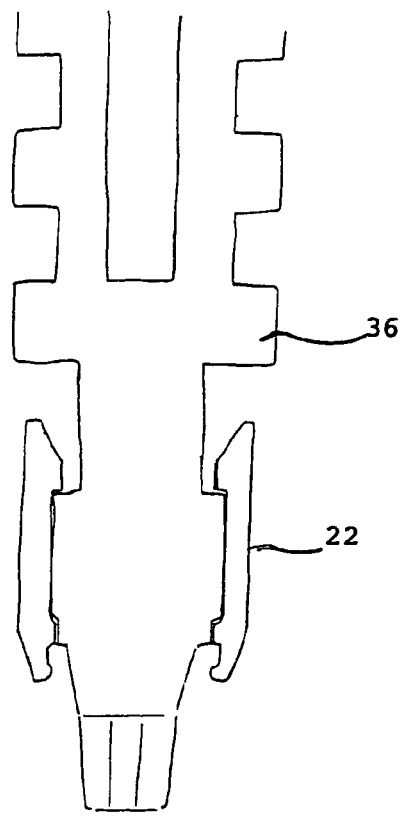
Figure 16:
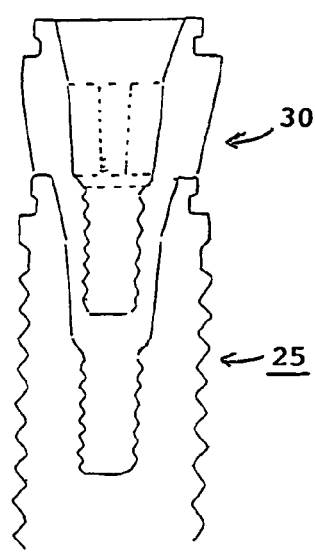

The connecting part 22 also enables a transfer part 36 to be fixed in reversible manner to an implantable element during the different steps of taking an imprint. Thus, in a first step, the transfer part 36 is, for example, fixed onto an intermediate pillar 30 by means of the connecting part 22, the intermediate pillar 30 itself being arranged on a dental implant 25 (FIG. 16). The connecting part 22 is placed on the external complementary part of a transfer part 36, by deformation followed by clipping. This external complementary part has the same shape as the complementary part of the placing tool 28, so as to be able to be clipped into the first and second grooves 12 and 23 of the connecting part 22. In order to be inserted in the bore 34 of the intermediate pillar 30, the transfer part 36 also comprises an end having a complementary shape to the shape of the bore 34 of the intermediate pillar 30. Reversible fixing of the transfer part onto the intermediate pillar is achieved by clipping the connecting part 22 onto the end of the intermediate pillar 30. The transfer part 36 also has an end identical to the bore 26 of the dental implant, so that the connecting part 22 can be clipped directly onto the dental implant. This avoids, in particular, having to perform screwing and unscrewing operations when taking imprints, resulting in time saving and a greater ease of execution.

Figure 17:
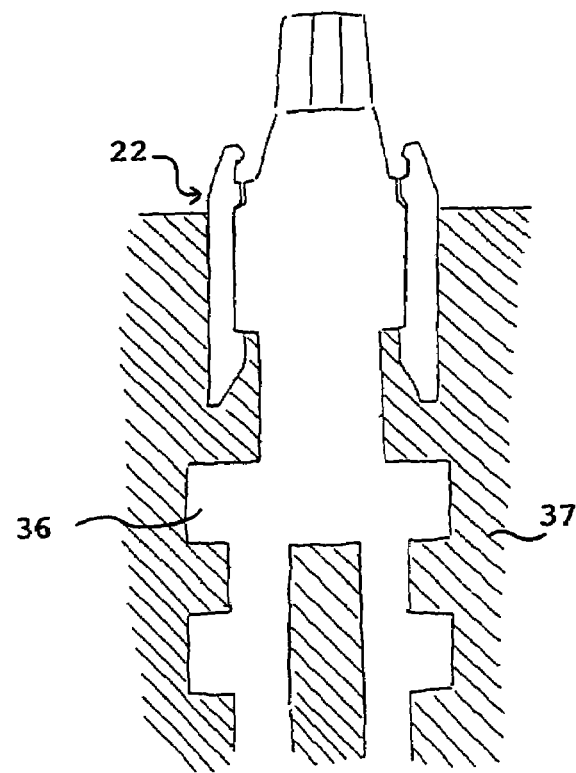
Figure 18:
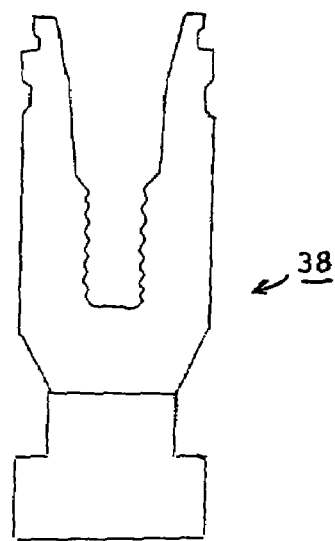
Figure 19:
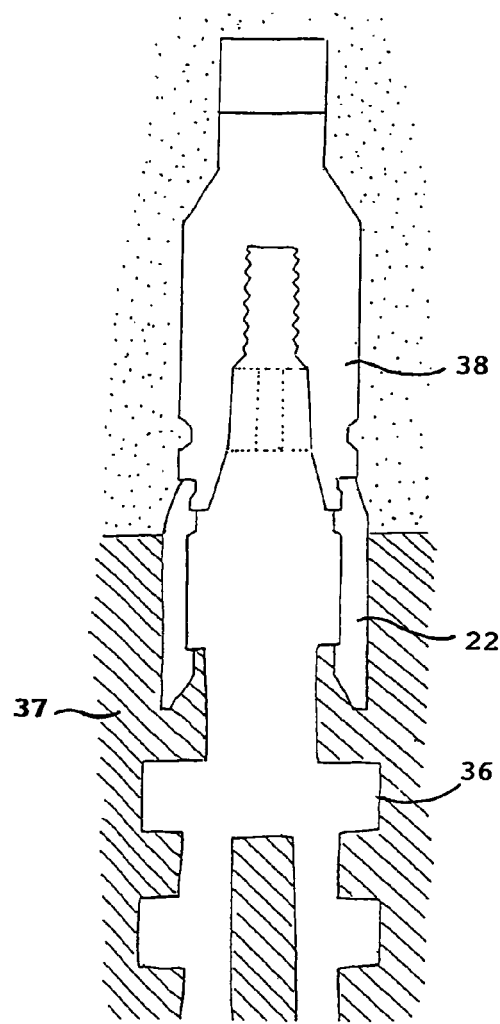
Figure 20:
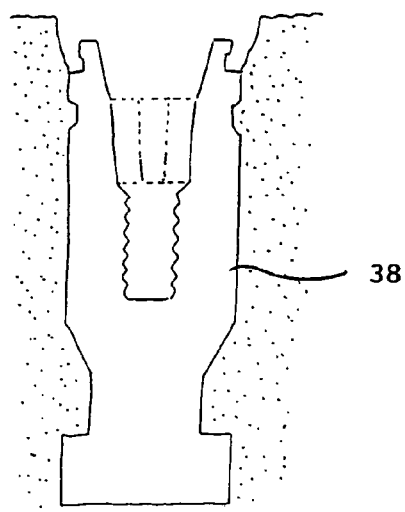
Figure 21:
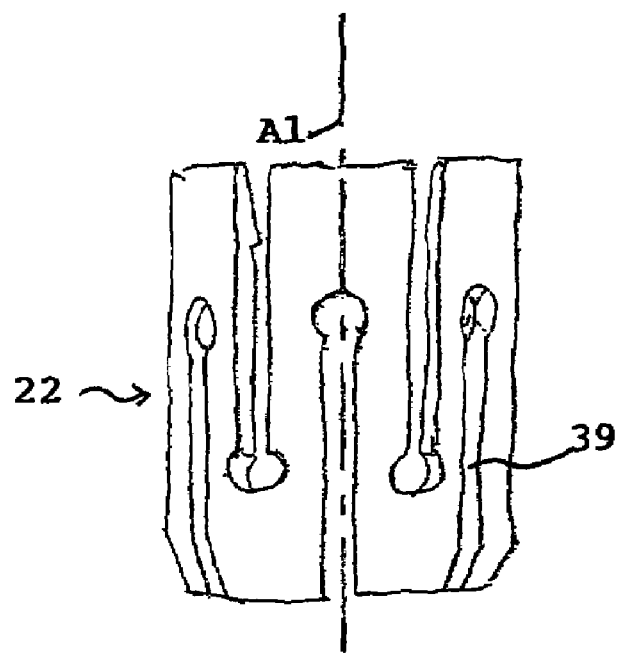

Once the transfer part has been fixed to the intermediate pillar 30, the practitioner makes an imprint of the transfer part by means of a closed imprint holder and an imprint material, and he then removes the imprint holder by unclipping the connecting part and the intermediate pillar. The transfer part 36 equipped with the connecting part 22 remains imprisoned in the imprint material 37 (FIG. 17). In a second step, the transfer part 36 is fixed to a die 38 (FIGS. 18 and 19), by means of the connecting part 22, the die 38 being a reproduction of the dental implant and of the intermediate pillar 30.

The connection mode by clipping by means of an intermediate connecting part thus enhances safety during surgical and prosthetic operations, in particular, while at the same time reducing the risks of ingestion of the instruments or of the prosthetic components. It also enables the different steps of fitting a dental prosthesis to be made easier, by eliminating the screwing and unscrewing phases of the tools on the implantable elements. This connection mode is also economical as the number of parts required when fitting a dental prosthesis is considerably reduced. Moreover, the connecting part is the only part among the tools to be in contact with the peri-implanting tissues. The connecting part is a single-use part, i.e. it is used for a single patient, but it can be used to connect several elements during the same session, when implants are fitted and for achieving the dental prosthesis.

Figure 22:
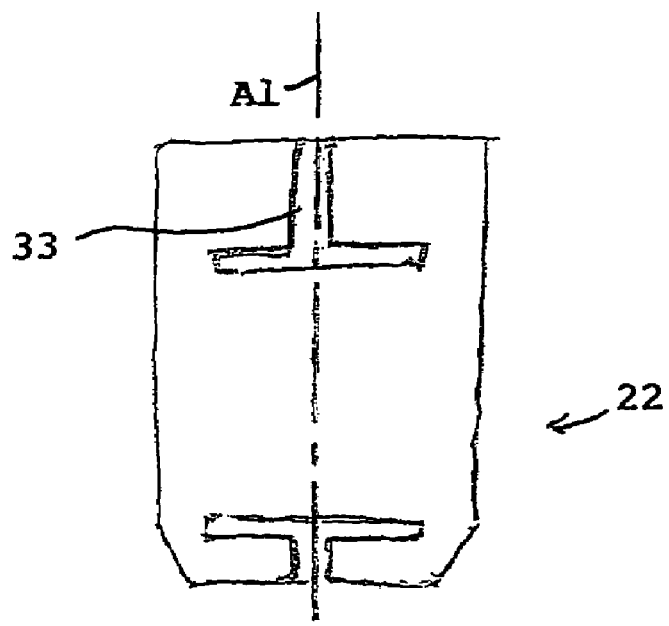
Figure 23:
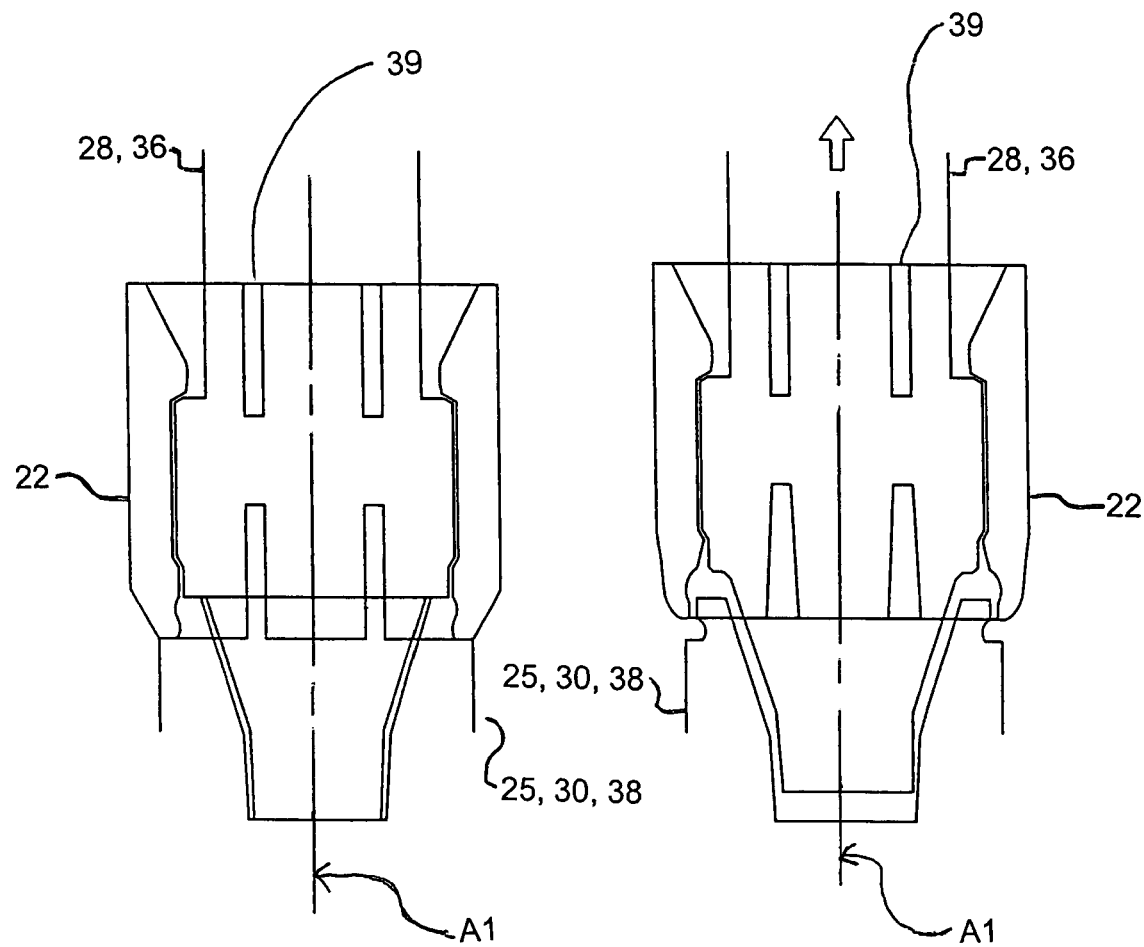
Figure 24:
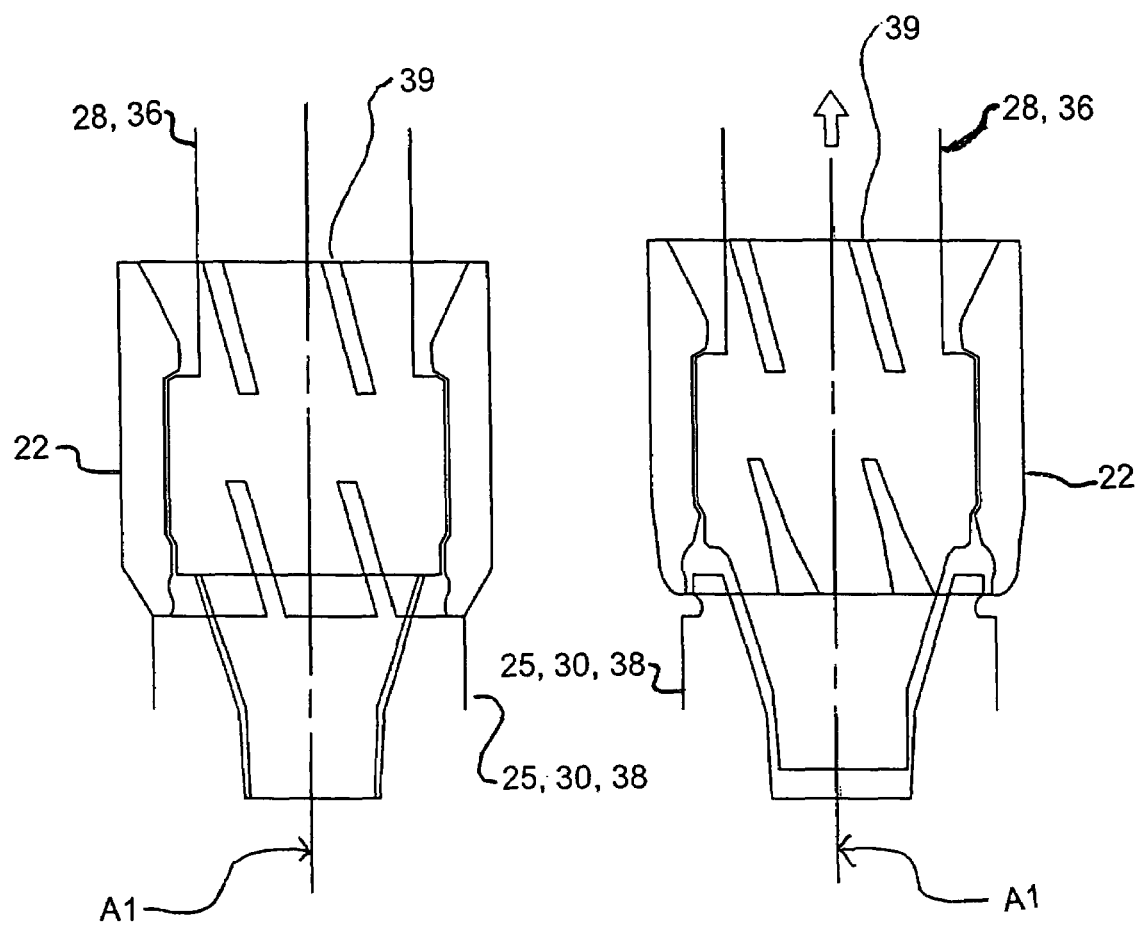
Figure 25:
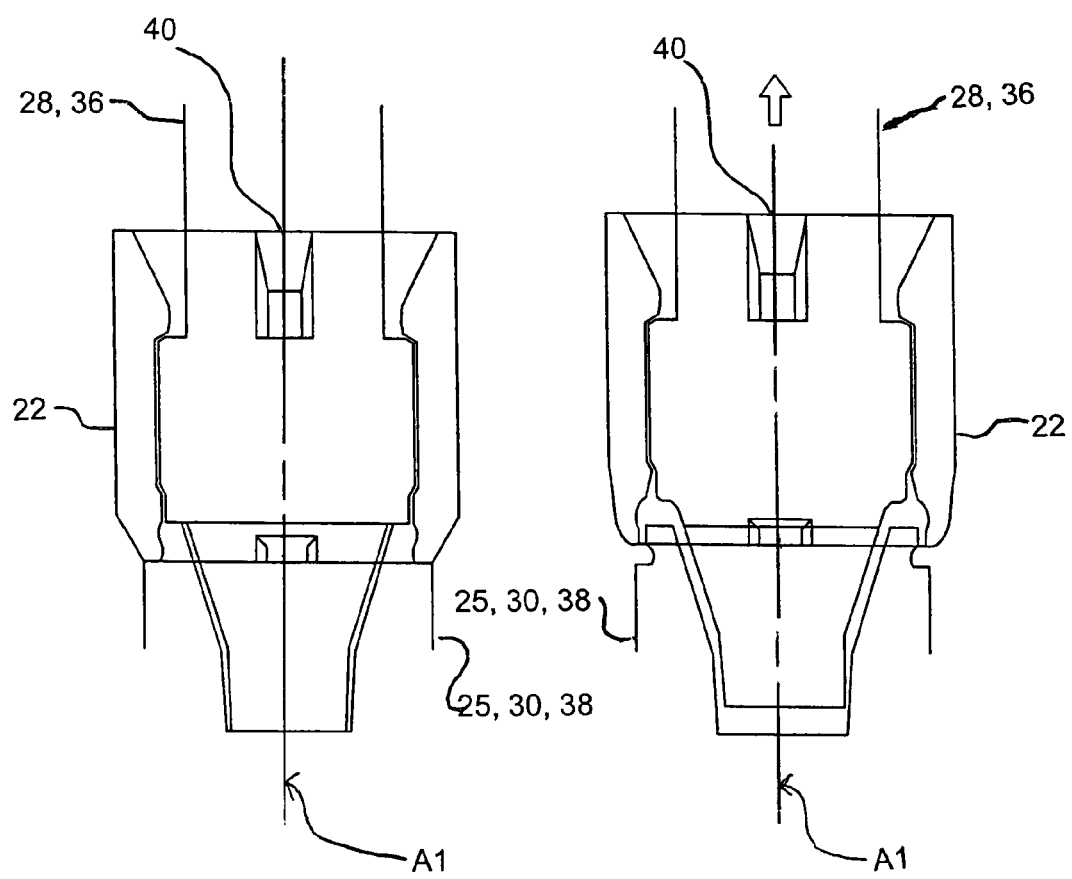

To be able to be clipped onto a tool, the intermediate connecting part must present elastic deformation properties. Thus, it can be made of plastic or metallic material or comprise a plastic part and a metal part. For a metallic connecting part, the latter comprises slots designed to make it deformable. Thus, the connecting part can comprise, at both ends thereof, regularly arranged slots 39 extending towards the centre of the part (FIGS. 21 to 25). For example, the slots can be longitudinal and extend towards the centre of the part (FIG. 21) or they can be T-shaped (FIG. 22). In FIGS. 23 and 24, the slots 39 are respectively parallel and oblique with respect to the axis A1 of the connecting part. The internal wall of the connecting part can also comprise at least two spigots 40 respectively arranged at one end of the connecting part, so as to strengthen the hold of the tool whereon the connecting part is placed (FIG. 25). An intermediate connecting part, made of plastic, can also comprise slots designed to enhance the elastic deformation capacity of the connecting part.

Reversible fixing of the intermediate connecting part onto the tool can also be performed by screwing. Thus, as represented in FIGS. 26 and 27, the internal wall of a hollow intermediate connecting part 41 comprises an internal thread 42 into which the threaded distal part 43 of a tool 44 is screwed, said threaded distal part forming the external complementary part of the tool. The intermediate connecting part 41 also comprises a groove 45 designed to cooperate by clipping with an external rib of an implantable element.

The invention is not limited to the embodiments described above. Indeed, the transfer part can either be fixed directly to the dental implant or be fixed onto an intermediate pillar. Furthermore, all of the implantable elements and the tools can be of any known type. According to the invention, they must, however, comprise an external complementary part designed to be fixed in reversible manner to the connecting part. For example, it is possible to use a transfer part according to the prior art, provided that it comprises an external complementary part designed to be fixed, in reversible manner, with the intermediate connecting part, for example by clipping or screwing. Finally, the connecting part is not limited to a cylindrical connecting part, and it can, for example, be polygonal, conical or cylindrical-conical. In the case of a conical or cylindrical-conical connecting part, reversible fixing is performed on the distal part of the tool only. The connecting part can also comprise an opening passing through the surface thereof in a direction parallel to the axis A1 of the connecting part so as to insert the connecting part laterally onto the distal part of the tool.

The invention claimed is:

1. A method for reversible fixing of a tool to an end of an implantable element, when fitting a dental prosthesis, the method successively comprising:
    reversibly fixing a hollow intermediate connecting part onto an external complementary part of the tool, the hollow intermediate connecting part and the external complementary part of the tool cooperating to prevent longitudinal movement of the tool relative to the hollow intermediate connecting part while they are reversibly fixed together; and
    thereafter positioning the tool, which has the hollow intermediate connecting part reversibly fixed thereto, with respect to the end of the implantable element until the hollow intermediate connecting part clips to the end of the implantable element with an end of the tool in direct contact with the implantable element,
    the implantable element having a head, a body and a groove positioned axially therebetween, the body configured to extend axially from the groove and into a body of a patient, and
    the hollow intermediate connecting part configured to be received by the groove of the implantable element and further configured to contact the groove of the implantable element at an edge of the hollow intermediate connecting part that is axially closest to the body of the implantable element.

2. The method according to claim 1, wherein the hollow intermediate connecting part comprises:
    a first clip configured to reversibly fix the hollow intermediate connecting part onto an external complementary part of the tool and to prevent longitudinal movement of the tool relative to the hollow intermediate connecting part while they are reversibly fixed together; and a second clip configured to clip to a complementary part of the implantable element, so as to enable reversible fixing of the tool to and in direct contact with the implantable element.

3. The method according to claim 2, wherein the first clip comprises at least one groove formed in an internal wall of the hollow intermediate connecting part and designed to cooperate by clipping with a salient peripheral rib on the tool.

4. The method according to claim 3, wherein the groove of the first clip is delimited by at least one rim arranged at one end of the hollow intermediate connecting part, the rim being designed to cooperate by clipping with the groove formed at the end of the implantable element.

5. The method according to claim 3, wherein the hollow intermediate connecting part comprises a second groove formed in the internal wall and configured to cooperate with an external rib formed at the end of the implantable element.

6. The method according to claim 1, wherein the hollow intermediate connecting part is made of plastic.

7. The method according to claim 1, wherein the hollow intermediate connecting part is made of metal and includes slots configured to make the hollow intermediate connecting part deformable.

8. The method according to claim 7, wherein the slots are T-shaped.

9. The method according to claim 7, wherein the slots are parallel to a longitudinal axis of the hollow intermediate connecting part.

10. The method according to claim 7, wherein the slots are oblique with respect to an axis of the hollow intermediate connecting part.

11. The method according to claim 1, wherein the hollow intermediate connecting part includes a metal part and a plastic part.

12. The method according to claim 1, wherein the hollow intermediate connecting part includes an opening passing through a surface thereof in a direction parallel to the longitudinal axis.

13. The method according to claim 1, wherein the hollow intermediate connecting part includes spigots salient towards the inside of the hollow intermediate connecting part.

14. The method according to claim 1, wherein the implantable element is selected from the group consisting of a dental implant, an intermediate pillar and a die.

15. The method according to claim 1, wherein the tool is a placing tool for placing the implantable element.

16. The method according to claim 1, wherein the tool is a transfer part and the implantable element is selected from the group consisting of a dental implant, an intermediate pillar and a die.

17. The method according to claim 1, wherein the end of the implantable element to which the hollow intermediate connecting part clips comprises an anti-rotational system, and the end of the tool is positioned in direct contact with and cooperates with the anti-rotational system when the hollow intermediate connecting part is clipped to the anti-rotational system.

18. The method according to claim 17, wherein the anti-rotational system is on an external portion of the implantable element, and the end of the tool receives the anti-rotational system during the positioning step.

19. The method according to claim 17, wherein the anti-rotational system is in an internal portion of the implantable element, and the end of the tool is received by the anti-rotational system during the positioning step.

20. The method according to claim 1, wherein a radial width of the head is smaller than a radial width of the body of the implantable element.

* * * * *